United States Patent [19]

Krepelka et al.

[11] Patent Number: 4,661,297

[45] Date of Patent: Apr. 28, 1987

[54] BASIC ETHERS OF 7-OXO-7H-BENZO(C) FLUORENE AND A PROCESS FOR THEIR PRODUCTION

[75] Inventors: Jiri Krepelka; Iva Vancurova; Karel Rezabek, all of Prague; Milan Melka, Hradec Kralove; Vojtech Pujman; Stanislava Pokorna, both of Prague; Ruzena Reichlova; Slavjanka Cernochova, both of Prague, all of Czechoslovakia

[73] Assignee: SPOFA, spojene podniky pro zdravotnickou vyrobu, Prague, Czechoslovakia

[21] Appl. No.: 417,834

[22] Filed: Sep. 14, 1982

Related U.S. Application Data

[63] Continuation-in-part of Ser. No. 231,411, Feb. 4, 1981, abandoned.

[30] Foreign Application Priority Data

Feb. 4, 1980 [CS] Czechoslovakia ............... 753-80

[51] Int. Cl.$^4$ .................................................. C07C 93/06
[52] U.S. Cl. ................................ 260/501.18; 564/352; 564/353; 564/354

[58] Field of Search .................. 564/352, 353, 354; 424/316, 330; 260/501.18

[56] References Cited

U.S. PATENT DOCUMENTS

| | | | |
|---|---|---|---|
| 2,820,817 | 1/1958 | Sam | 564/352 X |
| 3,350,405 | 10/1967 | Schulenberg et al. | 564/352 X |
| 3,592,819 | 7/1971 | Fleming et al. | 564/352 X |
| 3,707,471 | 12/1972 | Albrecht et al. | 564/352 X |
| 3,892,776 | 7/1975 | Hook et al. | 564/352 X |
| 4,169,897 | 10/1979 | Meyer et al. | 564/352 X |

FOREIGN PATENT DOCUMENTS 2068374 8/1981 United Kingdom .

*Primary Examiner*—Robert V. Hines

[57] ABSTRACT

Basic ethers of 7-oxo-7H-benzo(c) fluorene have been shown to evidence a pronounced antineoplastic and immunosuppressive effect in mammals suffering from leukemia. The technique for preparing the described ethers and the addition salts thereof with pharmaceutically acceptable organic and inorganic acids involves the aminoalkylation of 5-hydroxy-7-oxo-7H-benzo(c) fluorene and its corresponding nuclear substituted derivatives on the hydroxylic oxygen atom.

15 Claims, No Drawings

BASIC ETHERS OF 7-OXO-7H-BENZO(C) FLUORENE AND A PROCESS FOR THEIR PRODUCTION

This application is a continuation-in-part of our copending application Ser. No. 231,411, filed Feb. 4, 1981 and now abandoned.

This invention relates to basic fluorene ethers. More particularly, the present invention relates to basic ethers of 7-oxo-7H-benzo(c) fluorene, the addition salts thereof with a pharmaceutically acceptable inorganic or organic acid and to a method for the preparation thereof.

The novel compounds described herein have been found to evidence useful anti-tumor and immunosuppressive activities and may desirably be utilized as pharmaceuticals for treating leukemia in mammals.

The ethers described herein are of the formula

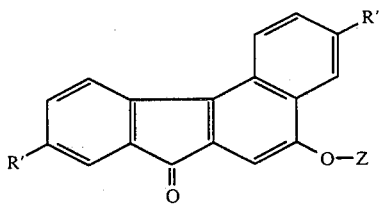

wherein R' is selected from the group consisting of a hydrogen atom, a methyl group and an ethyl group, and Z represents a group of the formula

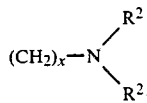

wherein x is an integer of 2 or 3 or is represented by a group of the formula

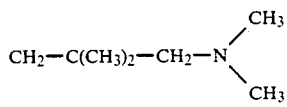

and $R^2$ is selected from among methyl or ethyl groups. It will also be appreciated that the present invention also relates to the pharmaceutically acceptable inorganic or organic acid addition salts of the foregoing ethers.

The compositions of the invention may conveniently be prepared by reaction of the compound

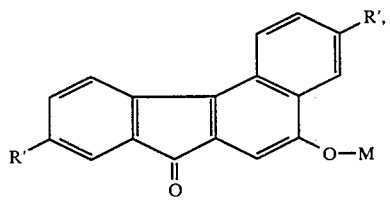

wherein R' is as designated above and M represents an alkali metal selected from among sodium and potassium, with a compound of the formula

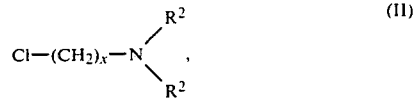

wherein $R^2$ and x are as represented above. Alternatively, the reactant designated (2) may be replaced by the following compound

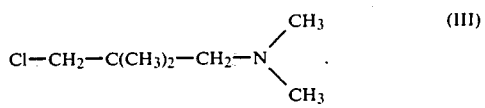

Reaction proceeds by adding from 1 to 3 molar equivalents of reactant (2) or (3) and effecting reaction in an anhydrous inert organic solvent. Solvents found to be particularly suitable for this purpose may be selected from among the aromatic hydrocarbons such as benzene toluene and xylene, or from among chlorinated hydrocarbons such as chloroethane and tetrachloroethane. A general preference has been found to exist, from the standpoint of yield, for toluene and chlorobenzene. The reaction is normally effected at the boiling temperature of the solvent.

Alternatively, this reaction may be effected in a two-phase system including an inert, water immiscible organic solvent and an aqueous alkali metal hydroxide solution at the boiling temperature of the reaction mixture. The inert solvents are as described above, toluene again being found preferable. The hydroxides suitable for this purpose are selected from among the hydroxides of sodium and potassium. This two-phase reaction may also be conducted with the aid of phase transfer catalysts.

The reactant designated (1), above, may conveniently be obtained from compounds of the formula

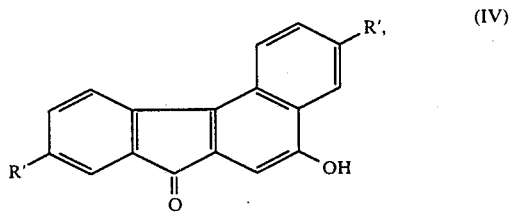

wherein R' is as represented above. This end may be attained by substituting an alkali metal atom for the hydrogen atom on the hydroxylic oxygen atom by conventional techniques in an aqueous or anhydrous reaction medium.

Following reaction, the resultant mixture is processed in accordance with known techniques, as for example, those described by Andrews et al, N. Med. Chem. 17, 882 (1974). The crude reaction product may then be purified by crystallization from a solvent or solvent mixture and characterized in the form of a base. Alternatively the reaction product may be treated with an excess, typically 10%, of a pharmaceutically acceptable inorganic or organic acid in an alcohol medium such as methanol or ethanol, to yield the corresponding addition salt which may be purified by crystallization from a suitable solvent.

Acids found suitable for preparing the addition salts include hydrochloric acid, sulfuric, phosphoric, maleic, tartaric, methane, and ethanesulfonic, napsylic, fumaric and citric acids.

Several examples of the present invention are set forth herein below. It will be appreciated by those skilled in the art that these examples are solely for purposes of exposition and are not to be construed as limiting. It should also be understood that the melting temperatures were determined with the Kofler apparatus and are uncorrected, and that the temperature values are expressed in degrees centigrade.

EXAMPLE 1

This example describes the preparation of 5-[2-(dimethylamino)ethoxy]-7-oxo-7H-benzo(c) fluorene.

150 ml of chlorobenzene and 14.8 grams (0.06 mole) of 5-hydroxy-7-oxo-7H-benzo(c) fluorene were added to a sodium methylate solution prepared by dissolving 2.76 grams (0.12 mole) of sodium in 45 ml of methanol. The reaction mixture was gradually warmed to the boiling temperature of chlorobenzene while simultaneously distilling off methanol. Then, a solution of 13.0 grams (0.12 mole) of 2-(dimethylamino)ethylchloride in 30 ml of chlorobenzene was added and the reaction mixture refluxed for 5 hours. Following cooling and decomposition with water, the organic layer was separated, extracted with a 10% potassium hydroxide solution, dried over anhydrous sodium sulfate and evaporated to dryness. The crystalline residue was purified by crystallization from a tetrachloromethane-hexane (1:1) mixture to yield 14.8 grams (78.3%) of the desired product which melted at a temperature of 91-93 degrees C.

EXAMPLE 2

This example describes the preparation of 5-[2-dimethylamino)ethoxy]-7-oxo-7H-benzo(c) fluorene hydrogen maleate.

A solution of 318 mg (1 millimole) of the product produced in example 1 in 5 ml of methanol was added to 127 mg (1.1 millimole) of maleic acid. Upon cooling to −5 degrees C., the precipitated solid was isolated by suction and crystallized from ethanol to yield the desired product which melted at a temperature of from 119°-124 degrees C.

This procedure was repeated to obtain the following products
(a) 5-[2-(dimethylamino)ethoxy]-7-oxo-7H-benzo(c) fluorene napsylate, m.p. 85°-87 degrees C. (crystallized from ethanol) and,
(b) 5-[2-(dimethylamino)ethoxy]-7-oxo-7H-benzo(c) fluorene hydrochloride, m.p. 268°-269 degrees C. (crystallized from ethanol).

EXAMPLE 3

This example describes the preparation of 3,9-diethyl-5-[2-(dimethylamino)ethoxy]-7-oxo-7H-benzo(c) fluorene hydrochloride.

50 ml of chlorobenzene and 6.04 grams (0.02 mole) of 3,9-diethyl-5-hydroxy-7-oxo-7H-benzo(c) fluorene were added to a sodium methylate solution prepared by dissolving 0.92 grams (0.04 mole) of sodium in 15 ml of methanol and the reaction carried out as described in example 1, 4.3 grams of 2-(dimethylamino)ethylchloride being employed. The resultant crude product melting at 88-90 degrees C. was dissolved in ethanol and acidified with an ethanolic hydrochloric acid solution. Upon cooling, a crystalline solid precipitated which was separated by suction and purified by crystallization from ethanol to yield 6.2 grams (76%) of the desired product which melted at a temperature of 241-243 degrees C.

The foregoing procedure was also used to obtain 3,9-dimethyl-5-[2-(dimethylamino)ethoxy]-7-oxo-7H-benzo(c) fluorene hydrochloride melting at 250-252 degrees C. and crystallized from an ethanol-hexane mixture.

EXAMPLE 4

This example describes the preparation of 5-[2-(diethylamino ethxy]-7-oxo-7H-benzo(c) fluorene hydrochloride.

A mixture containing 320 ml of toluene and 80 ml of water containing 13.2 grams (0.24 mole) of potassium hydroxide had added thereto 9.84 grams (0.04 mole) of 5-hydroxy-7-oxo-7H-benzo(c) fluorene and 14.9 grams (0.088 mole) of 2-(diethylamino)ethylchloride hydrochloride. The reaction mixture was refluxed for 12 hours and, on cooling, the toluene layer separated from the aqueous layer and processed in the manner described in examples 1 and 3. Crystallization of the crude product from ethanol yielded 13.6 grams (89.5%) of the desired compound which melts at 248-250 degrees C.

The foregoing procedure was used to prepare the following compounds:
(a) 3,9-dimethyl-5-[2-diethylamino)ethoxy]-7-oxo-7H-benzo(c) fluorene hydrochloride melting at 251-253 degrees C. and being crystallized from an ethanol-hexane mixture.
(b) 5-[3-(dimethylamino)propoxy]-7-oxo-7H-benzo(c) fluorene hydrochloride melting at 242-244 degrees C. and being crystallized from an ethanol-tetrachloromethane mixture.
(c) 3,9-diethyl-5-[2-(diethylamino)ethoxy]-7-oxo-7H-benzo(c) fluorene hydrochloride melting at 190-192 degrees C. and being crystallized from an ethanol-hexane mixture.
(d) 5-[3-(dimethylamino)-2,2-dimethylpropoxy]-7-oxo-7H-benzo(c) fluorene hydrochloride melting at 216-218 degrees C. and being crystallized from a methanol-acetone mixture, and
(e) 5-[2-(dimethylamino)ethoxy]-7-oxo-7H-benzo(c) fluorene hydrochloride melting at 268-269 degrees C. and being crystallized from ethanol.

The therapeutic effect of the described compounds on transplanted tumors in experimental animals is shown in Tables 1-3, on the following five pages.

In Table 4, the effect of Tiloron (NSC 143969; 2,7-bis-[2-(diethylamino)ethoxy]fluorene-9-one) and 5-(2-dimethylaminoethoxy)-7-oxo-7H-benzo(c) fluorene hydrochloride are compared on incorporation of $^{14}C$-adenine and $^{14}C$-valine with the cellular fraction of Ehrlich's ascitic carcinoma (insoluble in trichloacetic acid). The tests in vitro reveal that the composition of the invention was more than 10 times as effective as Tiloron. The inhibition of incorporation of adenine and valine into the used system of tumor cells is considered as an indication of an anti-tumorous, cytostatic action. This biological activity of the described compound is considerably greater than that of its congener Tiloron. (See also Table 4.)

This substance (identified as 13468) also evidenced immunosuppressive effects on antibody formation in mice (see Table 5), and inhibition of the formation of immunological serum anti-bodies. (see also Table 5.)

Explanations to Tables 1-3

& = statistically significant differences versus control at P=0.05
K = control
La: La leukaemia in mice $C_{57}Bl$
$L_{1210}$: Leukaemia growing in the form of ascitic tumors in hybrid DBA/H mice
$Sa_{37}$: Ascitic tumors in H mice
HK: Solid tumors, originally spontaneous mammary-gland adenocarcinoma in H mice
$Kr_2$: Krebs' ascitic tumor in H mice
EST: Ehrlich's solid tumor in H mice
Y: Yoshida's ascitic tumor in Wistar rats
13466: 5-(3-Dimethylaminopropoxy)-7-oxo-7H-benzo(c) fluorene hydrochloride
13467: 5-(3-Dimethylamino-2,2-dimethylpropoxy)-benzo(c) fluorene hydrochloride
13468: 5-(2-Dimethylaminoethoxy)-7-oxo-7H-benzo(c) fluorene hydrochloride

TABLE I

Effect of substance 13466 on course of transplanted tumours in experimental animals

| Species | Tumour | Route of adminin. | No. of partial doses | Partial dose in mg/kg | Total | Days of injection (after transplantation) | Day of tumour size assessment | Relative tumour size (% of control value) | Survival time of animals with respect to geom. mean | median |
|---|---|---|---|---|---|---|---|---|---|---|
| Mouse | LA | s.c. | 1× | 200 | 200 | 3 | — | — | — | 113%& |
|  | HK | s.c. | 8× | 50 | 400 | 5-10,12,13 | 14 | 66% | 121%& |  |
|  |  | o. | 8× | 50 | 400 | 5-10,12,13 | 14 | 82% | 131%& |  |
|  |  | o. | 8× | 100 | 800 | 5-10,12,13 | 14 | 76% | 112%& |  |
| Rat | Y | s.c. | 5× | 50 | 250 | 1-5 | — | — | 177%& |  |
|  |  | o. | 5× | 100 | 500 | 1-5 | — | — | 135%& |  |

TABLE II

Effect of substance 13467 on course of transplanted tumours in experimental animals

| Species | Tumour | Route of adminin. | No. of partial doses | Partial dose in mg/kg | Total | Days of injection (after transplantation) | Day of tumour size assessment | Relative tumour size (% of control value) | Survival time of animals with respect to geom. mean | median |
|---|---|---|---|---|---|---|---|---|---|---|
| Mouse | LA | s.c. | 1× | 300 | 300 | 3 | — | — | — | 186%& |
|  | L 1210 | s.c. | 1× | 250 | 250 | 1 | — | — | — | 135%& |
|  | HK | s.c. | 8× | 25 | 200 | 5-10,12,13 | 14 | 45%& | 89% |  |
| Rat | Y | s.c. | 5× | 50 | 250 | 1-5 | — | — | 232%& |  |
|  |  | o. | 5× | 100 | 500 | 1-5 | — | — | 256%& |  |

TABLE III

Effects of substance 13466 on course of transplanted tumours in experimental animals

| Species | Tumour | Route of admin. | No. of partial doses | Partial dose in mg/kg | Total | Days of injection (after transplantation) | Day of tumour size assessment | Relative tumour size (% of control value) | Survival time of animals with respect to geom. mean | median | % of animals surviving day 35 after transplantation |
|---|---|---|---|---|---|---|---|---|---|---|---|
| Mouse | La | s.c. | 1× | 250 | 250 | 3 | — | — | — | 500%& |  |
|  | L 1210 | s.c. | 6× | 50 | 300 | 1;5;8;12;15;19; | — | — | — | 117%& |  |
|  |  | s.c. | 6× | 75 | 450 | 1;5;8;12;15;19; | — | — | — | 142%& |  |
|  |  | s.c. | 6× | 100 | 600 | 1;5;8;12;15;19; | — | — | — | 142%& |  |
|  |  | s.c. | 6× | 125 | 750 | 1;5;8;12;15;19; | — | — | — | 168% |  |
|  | Sa 37 | p.o. | 3× | 75 | 225 | 1,4,7 | 10 | 92% | — | 123%& |  |
|  | Kr 2 | p.o. | 2× | 150 | 300 | 1,8 | 10 | 62%& | — | 128%& |  |
|  | HK | s.c. | 8× | 50 | 400 | 5-10,12,13 | 14 | 58%& | 107% |  |  |
|  |  | p.o. | 8× | 50 | 400 | 5-10,12,13 | 14 | 73%& | 102% |  |  |
|  |  | p.o. | 4× | 100 | 400 | 5,7,9,12 | 14 | 48%& | 125%& |  |  |
|  |  | p.o. | 2× | 150 | 300 | 5,12 | 14 | 65%& | 123%& |  |  |
|  | EST | p.o. | 4× | 50 | 200 | 5,7,9,12 | 14 | 77%& | 135%& |  |  |
|  |  | p.o. | 4× | 100 | 400 | 5,7,9,12 | 14 | 70%& | 134%& |  |  |
| Rat | Y | s.c. | 5× | 50 | 250 | 1-5 | — | — | 103% |  |  |
|  |  | o. | 3× | 50 | 150 | 1,4,8 | — | — | 152%& |  | 50%(K = 0%)& |
|  |  | o. | 3× | 75 | 225 | 1,4,8 | — | — | 140%& |  | 40%(K = 0%)& |
|  |  | o. | 5× | 100 | 500 | 1-5 | — | — | 135%& |  |  |

TABLE IV

Effects of Tiloron and substance 13468 on incorporation of $^{14}$C-adenine and $^{14}$C-valine into cellular fraction of Ehrlichs ascitic carcinoma, insoluble in trichloroaectic acid, in vitro. Radioactivity incorporation expressed in cpm.
$IC_{50}$ = concentration inhibiting incorporation by 50 percent.

| Substance | Incorporated amino acid | 0 | 18,75 | 37,5 | 75 | 150 | 300 | 600 | IC$_{50}$ |
|---|---|---|---|---|---|---|---|---|---|
| Tiloron | Adenine | 1060 (100%) | — | 1160 (109%) | 1252 (118%) | 1096 (103%) | 979 (92%) | 563 (53%) | 600 μM |
|  | Valine | 2455 (100%) | — | 2395 (98%) | 2374 (97%) | 2247 (92%) | 2443 (100%) | 1944 (79%) | 600 μM |
| 13 468 HCl | Adenine | 1060 (100%) | 757 (71%) | 714 (87%) | 266 (25%) | 59 (6%) | — | — | 53 μM |
|  | Valine | 2455 (100%) | 2394 (98%) | 2253 (92%) | 887 (36%) | 349 (14%) | — | — | 65 μM |

TABLE V

Haemagglutanin and haemolysin titres in mouse serum on day 9 after ram rythrocyte immunization under effect of substance 13468. Substance injected subcutaneously 1× daily either for 5 days (2 days before, on day of, 2 days after immunization) or for 11 days (2 days before, on day of, 8 days after immunization). Groups of 12 animals each. Titre expressed by mean value of highest attenuation of serum eliciting complete agglutination or complete haemolysis.

| No. of doses | Partial dose (mg/kg) | Total dose (mg/kg) | Haemagglutinins Titre | % | Haemolysins Titre | % |
|---|---|---|---|---|---|---|
| 0 | 0 | 0 | 343 | 100% | 37 | 100% |
| 5× | 8 | 40 | 243 | 71% | 49 | 132% |
| 5× | 40 | 200 | 12 | 3.5% | Suppressed (under 10) | (under 27%) |
| 11× | 8 | 88 | 243 | 71% | Suppressed (under 10) | (under 27%) |
| 11× | 40 | 440 | Suppressed (under 10) | (under 2.9%) | Suppressed (under 10) | (under 27%) |

As employed herein, the term "treatment" is defined as the inhibition of characteristic disease symptoms in mammalian subjects bearing leukemic tumors, namely tumor growth, shortening of the survival period of biological subjects and increasing the number or growth of tumor cells.

Tumor growth may be observed clinically or in experiments in vivo, that is, with experimental animals, or in vitro, for example, in tissue cultures prepared from tumors. Assessment of tumor growth may be effected by measuring the weight of the tumor mass or, more effectively, by measuring the radioactivity after incorporation therein of certain substances of natural origin such as amino acids, adenine, thymidine and the like labelled with radioactive atoms such as $^{14}$C, $^3$H, etc.

Thus, by way of exemplification, the IC$^{50}$ values (inhibitory concentration which lowered the initial rate of $^{14}$C incorporation to 50% of control) are shown in Table VI, below (Yoshida's Tumor, (U-$^{14}$C) amino acid mixture)

TABLE VI

| Compound No. | Mo. Wt. | IC$_{50}$(μmol per liter) |
|---|---|---|
| 13466+ | 441.0 | 120 |
| 13467+ | 395.9 | 101 |
| 13468+ | 353.9 | 32 |
| Tiloron++ | 483.5 | 154 |

+ compound of invention described above
++ compound of prior art described by Munson et al. Cancer Res. 32, 1397, 1972.

The $IC_{50}$ values of compound 13468 are also shown in Table VII with varying substrates.

TABLE VII

| Substrate | IC$_{50}$ (μmol per liter) | Tumor |
|---|---|---|
| (thymine U-$^{14}$C) thymidine | 4 | Yoshida |
| 5-iodo-2-deoxy(6-$^3$H) uridine | 12 | Yoshida |
| (6-$^3$H) uridine | 36 (12.6 μg./ml.) | Yoshida |
| L-(U-$^{14}$C)amino acid mixture | 32 | Yoshida |
| L-(U-$^{14}$C)amino acid mixture | 31 | Ehrlich |
| L-(U-$^{14}$)leucine | 29 | Yoshida |

The foregoing data clearly indicate that the compounds of the invention are potent inhibitors of DNA, RNA and protein biosynthesis. This is of significance because the suppression of tumor cells in a host is attained by inhibition of the biosynthesis of DNA, RNA and proteins. The effect of the compounds of the invention on DNA, RNA and protein biosynthesis has been found to be comparable with that of clinically antitumor active drugs such as cytosine arabinoside, actinomycin D and CCNU. Data are set forth in Table VIII, below.

TABLE VIII

| Compound | Substrate | IC$_{50}$ |
|---|---|---|
| Cytosine arabinoside (NSC 63878) | (thymine-U-$^{14}$C)-thymidine | 2 μmol/liter |
| Cytosine arabinoside | L-(U-$^{14}$)amino-acid | 430 μmol/liter |
| Actinomycin D (NSC 3053) | (6-$^3$H)uridine | 1.7 μg/ml. |
| CCNU (NSC 79037) | L-(U-$^{14}$C)amino-acid mixture | 45 μmol/liter |

The anti-tumor compounds described herein have also been studied from the standpoint of toxicity and the conclusion drawn that they are not toxic to mammalian hosts. The toxicological data set forth in Table IX, below, supports this conclusion. This data was based upon treatment of mice S (males of 22-24 gram weight).

TABLE IX

| Compound No. | Administration | LD$_{50}$ mg/kg. |
|---|---|---|
| 13466 | subcutaneously | 320 |
| 13467 | subcutaneously | 550 |
| 13468 | subcutaneously | 490 |
| 13468 | intravenously | 90 |
| 13468 | orally | 600 |

The inhibitory in vivo effects on tumor growth exhibited by compounds of the invention in the absence of host toxicity have been theorized as being attributable to the increased susceptibility of tumor cells due to more rapid DNA biosynthesis exhibited by them than by host normal cells. These effects may be extrapolated to include other biological subjects of mammalian origin.

Thus, for example, it has been found that the sensitivity of human myelogenous leukemia cells was greater than that of animal tumor cells (DNA biosynthesis IC$_{50}$ was 5 μmol of compound 13468 per liter).

The dose for treating humans with the described compounds may conveniently be calculated from the results of in vivo experiments. The single dose of compound 13468 may range from 2.5 to 5.0 mg. per kg. of body weight orally (in capsule form), or from 0.4 to 2.0 mg. per kg. of body weight intravenously (slowly) dissolved in water, preferably during the infusion of saline or an isotonic solution of glucose. Doses may be adjusted to individual tolerance and responsiveness of each patient and type of leukemia.

Based upon the foregoing studies, it is concluded that the claimed compounds may effectively be used for treating mammalian leukemias.

We claim:

1. Basic ethers of 7-oxo-7H-benzo(c) fluorene of the formula

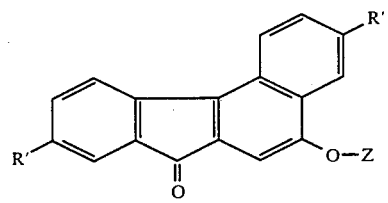

wherein R' is selected from the group consisting of hydrogen, a methyl group and an ethyl group, and Z is selected from the group consisting of

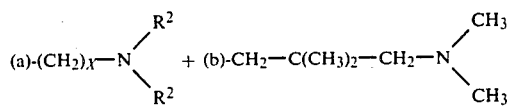

wherein R$^2$ is selected from the group consisting of a methyl group and an ethyl group, and x is an integer of 2-3.

2. The addition salt of the compound of claim 1, with a pharmaceutically acceptable acid.

3. Addition salt in accordance with claim 2, wherein said acid is an inorganic acid.

4. Addition salt in accordance with claim 2, wherein said acid is an organic acid.

5. 5-[2-(dimethylamino)ethoxy]-7-oxo-7H-benzo(c) fluorene.

6. 5-[2-(dimethylamino)ethoxy]-7-oxo-7H-benzo-(c) fluorene hydrochloride.

7. 5-[2-(dimethylamino)ethoxy]7-oxo-7H-benzo(c) fluorene napsylate.

8. 5-[2-(dimethylamino)ethoxy]-7-oxo-7H-benzo(c) fluorene hydrogen maleate.

9. 5-[2-(dimethylamino)ethoxy]7-oxo-7H-benzo(c) fluorene hydrochloride.

10. 5-[2-(dimethylamino)propoxy]-7-oxo-7H-benzo(c) fluorene hydrochloride.

11. 5-[3-(dimethylamino)-2,2-dimethylpropyl]-7-oxo-7H-benzo(c) fluorene hydrochloride.

12. 3,9-dimethyl-5-[2-(dimethylamino)ethoxy]-7-oxo-7H-benzo(c) fluorene hydrochloride.

13. 3,9-dimethyl-5-[2-(diethylamino)ethoxy]-7-oxo-7H-benzo(c) fluorene hydrochloride.

14. 3,9-diethyl-5-[2-(dimethylamino)ethoxy]-7-oxo-7H-benzo(c) fluorene hydrochloride.

15. 3,9-diethyl-5-[2-diethylamino)ethoxy]-7-oxo-7H-benzo(c) fluorene hydrocarbon.

* * * * *